(12) United States Patent
Chodkowski

(10) Patent No.: US 9,717,872 B2
(45) Date of Patent: Aug. 1, 2017

(54) INFLATABLE HEADGEAR FOR A PATIENT INTERFACE ASSEMBLY

(71) Applicant: KONINKLIJKE PHILIPS N.V., Eindhoven (NL)

(72) Inventor: Lauren Patricia Chodkowski, Pittsburgh, PA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 337 days.

(21) Appl. No.: 14/359,195

(22) PCT Filed: Nov. 14, 2012

(86) PCT No.: PCT/IB2012/056415
§ 371 (c)(1),
(2) Date: May 19, 2014

(87) PCT Pub. No.: WO2013/076624
PCT Pub. Date: May 30, 2013

(65) Prior Publication Data
US 2014/0261440 A1   Sep. 18, 2014

Related U.S. Application Data

(60) Provisional application No. 61/562,574, filed on Nov. 22, 2011.

(51) Int. Cl.
*A61M 16/06* (2006.01)

(52) U.S. Cl.
CPC .... *A61M 16/0627* (2014.02); *A61M 16/0683* (2013.01)

(58) Field of Classification Search
CPC .......... A61M 16/0627; A61M 16/0683; A61B 17/135; A62B 9/00; A62B 18/00; A62B 18/02; A62B 18/08; A62B 18/084
See application file for complete search history.

(56) References Cited

U.S. PATENT DOCUMENTS

| 3,599,636 A | * | 8/1971 | Gutman | A62B 18/084 128/207.11 |
| 4,466,145 A | * | 8/1984 | Jones | A61G 1/00 441/40 |
| 4,819,389 A | * | 4/1989 | Kihn | E04H 15/20 135/97 |

(Continued)

FOREIGN PATENT DOCUMENTS

| EP | 0032422 A1 | 7/1981 |
| EP | 0906038 B1 | 4/2003 |

(Continued)

*Primary Examiner* — Kathryn E Ditmer
(74) *Attorney, Agent, or Firm* — Michael W. Haas

(57) ABSTRACT

A patient interface device includes a headgear assembly (20) having at least two strap member (22). The strap members (22) each include a flexible body and a bladder assembly (50). In one embodiment, bladder assemblies (50) may be selectively inflated and deflated. In the inflated, or first, filled configuration, headgear assembly (20) defines a three-dimensional shape sized to fit about a patient's head. In the deflated, or second, collapsed configuration, the head gear assembly (20) may be placed in a flat or other compact configuration.

8 Claims, 8 Drawing Sheets

(56) References Cited

U.S. PATENT DOCUMENTS

| | | | | |
|---|---|---|---|---|
| 5,269,296 | A | * 12/1993 | Landis | A61M 16/0666 128/204.18 |
| 5,445,858 | A | * 8/1995 | Nwoko | A45F 3/12 428/174 |
| 6,471,105 | B1 | * 10/2002 | Ammerman | A45C 13/30 150/110 |
| 6,915,932 | B1 | * 7/2005 | Wolfe | A63B 55/408 2/268 |
| 2005/0109342 | A1 | 5/2005 | Easom | |
| 2006/0135873 | A1 | * 6/2006 | Karo | A61B 5/02233 600/499 |
| 2010/0224199 | A1 | * 9/2010 | Smith | A41D 13/1161 128/863 |
| 2011/0197341 | A1 | * 8/2011 | Formica | A61M 16/0683 2/209.3 |

FOREIGN PATENT DOCUMENTS

| | | | | |
|---|---|---|---|---|
| FR | 2859383 A1 | * 3/2005 | | A61M 16/06 |
| TW | 1267393 B | 12/2006 | | |
| WO | WO2005099801 A1 | 10/2005 | | |
| WO | WO 2011022779 A1 | * 3/2011 | | A61M 16/0066 |

* cited by examiner

INFLATABLE HEADGEAR FOR A PATIENT INTERFACE ASSEMBLY

CROSS-REFERENCE TO RELATED APPLICATIONS

This patent application claims the priority benefit under 35 U.S.C. §371 of international patent application no. PCT/IB2012/056415, filed Nov. 14, 2012, which claims the priority benefit under 35 U.S.C. §119(e) of U.S. Provisional Application No. 61/562,574 filed on Nov. 15, 2011, the contents of which are herein incorporated by reference.

BACKGROUND OF THE INVENTION

1. Field of the Invention

The present invention relates to patient interface devices for transporting a gas to and/or from an airway of a patient, and in particular, to a patient interface device having a shaped headgear component with an inflatable bladder assembly.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver continuous positive airway pressure (CPAP) or variable airway pressure, which varies with the patient's respiratory cycle or varies with the condition of the patient (e.g., snoring, apneas, hyponeas), to treat a medical disorder, such as sleep apnea syndrome, in particular, obstructive sleep apnea (OSA), or congestive heart failure.

Non-invasive ventilation and pressure support therapies involve the placement of a patient interface device including a patient sealing assembly, such as but not limited to, a mask component on the face of a patient. The mask component may be, without limitation, a nasal mask that covers the patient's nose, a nasal cushion having nasal prongs that are received within the patient's nares, a nasal/oral mask that covers the patient's nose and mouth, or a full face mask that covers the patient's face. The patient interface device interfaces the ventilator or pressure support device with the airway of the patient, so that a flow of breathing gas can be delivered from the pressure/flow generating device to the airway of the patient.

Typical designs for the mask component of a patient interface device include a faceplate or shell having a cushion or seal attached thereto which seals around the nose and in the case of a nasal/oral interface, also around the mouth of the patient. The mask is typically strapped to the head of the patient using a headgear assembly comprised of a number of non-elastic straps connected to the faceplate. The straps may be adjustable, so that the headgear assembly may be tightened or loosened to adjust the fit of the headgear assembly and mask. Alternatively, the headgear assembly may be made of, or include, elastic strap members. Such elastic members may also have an adjustable length.

Because such patient interface devices are typically worn for an extended period of time, it is important for the headgear component to maintain the mask component of the device in a tight enough seal against the patient's face without causing discomfort. That is, if the straps are adjusted so as to be overly tight, the headgear assembly produces uncomfortable pressure on portions of the patient's head (possibly resulting in red mark formation on the skin). However, if the headgear assembly is loosened, the mask may not remain sealed against the patient's face.

SUMMARY OF THE INVENTION

Accordingly, it is an object of the present invention to provide a patient interface device headgear assembly that overcomes the shortcomings of a conventional patient interface device headgear assembly. This object is achieved according to one embodiment of the present invention by providing a patient interface device headgear assembly wherein at least two of the strap members include a fluid filled bladder assembly. The fluid filled bladder assembly allows the headgear to maintain a semi-rigid three dimensional shape. The three dimensional shape of the headgear assembly allows a patient sealing assembly to be maintained in a selected relationship relative to the patient's face. That is, the patient sealing assembly is disposed adjacent a patient's nose and mouth without applying an uncomfortable pressure to the patient's head.

It is yet another object of the present invention to provide a method of selectively configuring a patient interface device headgear assembly, the headgear assembly structured to support a patient sealing assembly, the headgear assembly including a plurality of strap members, the strap members forming a web, at least two of the strap members structured to be coupled to the patient sealing assembly, a number of strap members in the plurality of strap members each having a bladder assembly, each bladder assembly structured to be selectively filled with, or emptied of, a fluid, whereby, when the bladder assembly is substantially filled with a fluid, the web defines a first, three-dimensional configuration, and, when the bladder assembly is substantially emptied of fluid, the web defines a second, collapsed configuration, the patient sealing assembly coupled to the at least two of the strap members structured to be coupled to the patient sealing assembly, the bladder assembly being in the second configuration initially, the method including the step of introducing a fluid into each bladder assembly until each bladder assembly is substantially filled.

In one embodiment, the fluid may be introduced to, or removed from, the bladder assembly. When the bladder assembly is substantially full, the plurality of straps, which may be identified as a "web," defines a first, three dimensional configuration. When the bladder assembly is substantially empty, the web defines a collapsed configuration. That is, in the collapsed configuration, the web may be placed in a substantially flat configuration.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
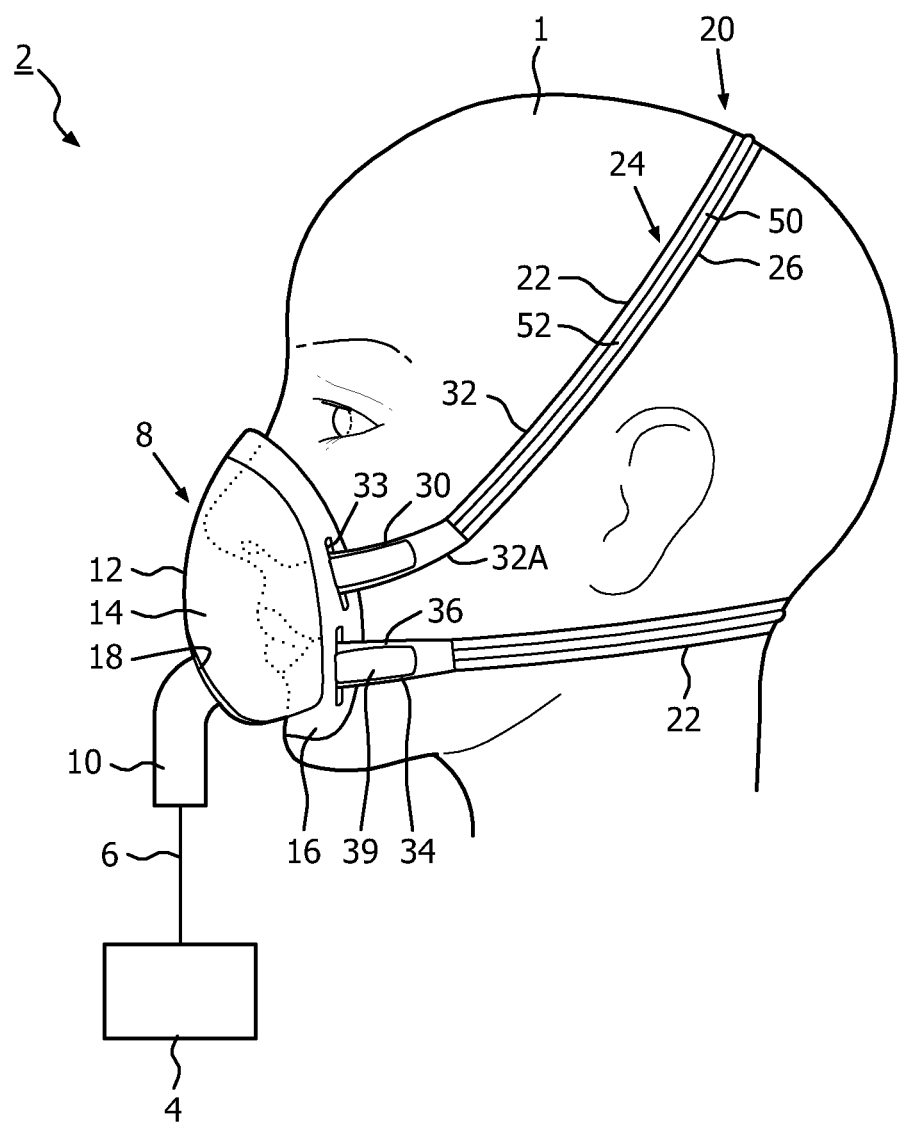
FIG. 1 is a schematic diagram of a system adapted to provide a regimen of respiratory therapy to a patient according to one exemplary embodiment of the present invention.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As used herein, a "substantially rigid" body or web is a body or web structured to maintain a three-dimensional shape without any additional support. That is, the "substantially rigid" body or web will not compress an object disposed within the body or web (unless that body is larger than the space defined by the body or web). It is noted that an elastic web, a web of tension members, or a web including tension members and elastic members, cannot be a "substantially rigid" body.

A system 2 adapted to provide a regimen of respiratory therapy to a patient according to one exemplary embodiment is generally shown in FIG. 1. System 2 includes a pressure generating device 4 (shown schematically), a delivery conduit 6 (shown schematically), and a patient interface device 8 having a fluid coupling conduit 10. Pressure generating device 4 is structured to generate a flow of breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, Pa.), and auto-titration pressure support devices. Delivery conduit 6 is structured to communicate the flow of breathing gas from pressure generating device 4 to patient interface device 8 through fluid coupling conduit 10, which in the illustrated embodiment is an elbow connector. Delivery conduit 6 and patient interface device 8 are often collectively referred to as a patient circuit.

As seen in FIG. 1, in the exemplary embodiment, patient interface device 8 includes a patient sealing assembly 12 and a headgear assembly 20. Patient sealing assembly 12 in the illustrated embodiment is a nasal/oral mask structured to fit over the nose and mouth of the patient 1. However, other types of patient sealing assemblies, such as, without limitation, a nasal mask, a nasal cushion, nasal cannula, a cradle mask, a nasal/oral mask or a total mask that covers face, which facilitate the delivery of the flow of breathing gas to the airway of a patient, may be substituted for patient sealing assembly 12 while remaining within the scope of the present invention. Patient sealing assembly 12 includes a frame member 14 having a cushion member 16 coupled thereto. Cushion member 16 may be inflatable.

In the illustrated embodiment, frame member 14 is made of a rigid or semi-rigid material, such as, without limitation, an injection molded thermoplastic or silicone, and may include a faceplate portion 18 having a central opening formed therein. As seen in FIG. 1, fluid coupling conduit 10 is coupled to faceplate portion 18 through the opening formed therein, which configuration allows the flow of breathing gas from pressure generating device 4 to be communicated to an interior space defined by cushion member 16, and then to the airway of a patient. In the illustrated embodiment, cushion member 16 is defined from a unitary piece of soft, flexible, cushiony, elastomeric material, such as, without limitation, silicone, an appropriately soft thermoplastic elastomer, a closed cell foam, or any combination of such materials.

Headgear assembly 20 includes a plurality of strap members 22 disposed relative to each other so as to form a web 24. As used herein, "strap members 22" are selectably rigid (as described below) members, or, semi-rigid members (as described below). Headgear assembly 20 may also include non-selectably rigid, or, non-semi-rigid members; as used herein, such members will be identified as "bands 23." Bands 23 may be elastic, flexible, and/or rigid. Various embodiments/patterns of webs 24 are shown in FIGS. 1, and 5-9, as discussed below.

Figure 2:
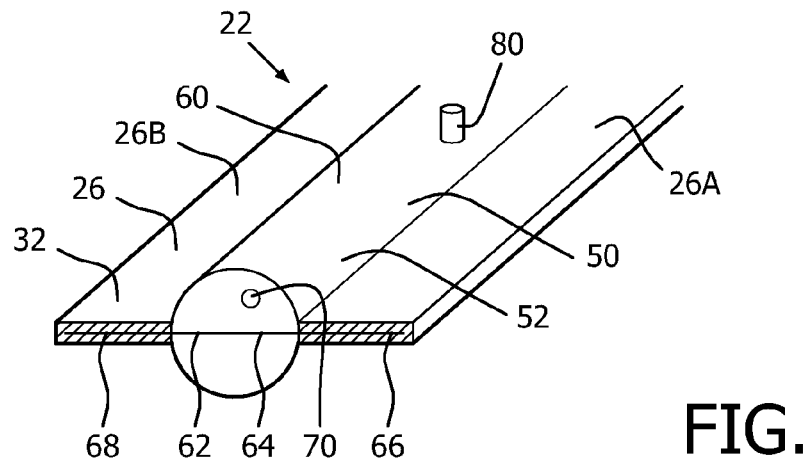
FIG. 2 is a cross-sectional view of a strap member.
Figure 3:
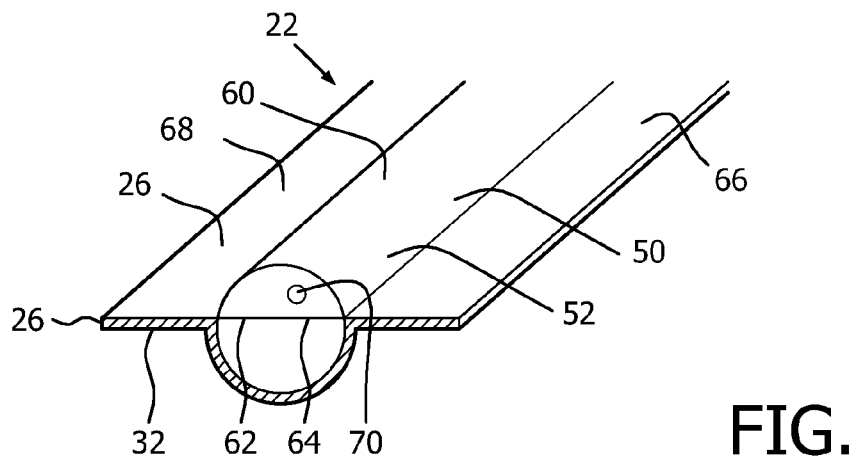
FIG. 3 is a cross-sectional view of an alternate strap member.
Figure 4:
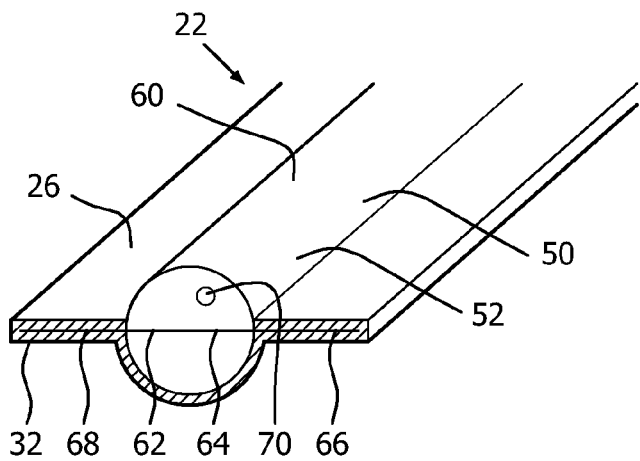
FIG. 4 is a cross-sectional view of an alternate strap member.

As shown in FIGS. 2-4, strap members 22 include an elongated body 26 and an elongated bladder assembly 50. Strap member bodies 26 have at least one layer of a flexible material 32. In the exemplary embodiment, strap flexible material 32 is non-elastic, soft, and breathes. That is, strap flexible material 32 allows air to pass therethrough. Strap body flexible material 32 may also be a non-slip material. The coupling of strap member bodies 26 to bladder assemblies 50 will be discussed below after an exemplary embodiment of bladder assemblies 50 is discussed.

As shown in FIG. 1, at least two of strap members 22 are structured to be coupled to patient sealing assembly 12. The at least two of strap members 22 extend from web 24 to a location adjacent the patient's nose and mouth. Where patient sealing assembly 12 is small, e.g. a nasal mask or a nasal cushion (not shown), there is one strap on each side of the patient's face extending toward the patient's nose and structured to be coupled to patient sealing assembly 12. As shown in the exemplary embodiment, when patient sealing assembly 12 is larger, such as a mask, there may be two strap members 22 on each side of the patient's face extending toward the patient's nose and structured to be coupled to patient sealing assembly 12. Having two connection points between headgear assembly 20 and patient sealing assembly 12 allows for greater control of the orientation of patient sealing assembly 12 on the patient's face.

Strap members 22 structured to be coupled to patient sealing assembly 12 may include a coupling device 30. Coupling device 30 may be a rigid coupling, such as, but not limited to, snaps, an epoxy, adhesive, or rigid clips (none shown). Alternatively, coupling device 30 may be a flexible coupling, such as, but not limited to, a slot 33 in frame member 14 and a flexible material 32A having a hook-and-loop fastener 34 disposed thereon. Coupling device flexible material 32A may be unitary with the strap member flexible material 32. That is, coupling device flexible material 32A may be the distal end of strap members 22 structured to be coupled to patient sealing assembly 12. A first portion of coupling device flexible material 32A has "hook" portion 36 of hook-and-loop fastener 34 disposed thereon and a second portion of coupling device flexible material 32A has "loop" portion 38 of hook-and-loop fastener 34 disposed thereon. First portion 36 is passed through slot 33 and folded over to be coupled with second portion 38. In another embodiment, coupling device flexible material 32A may be elastic. or. a portion of coupling device 30 between hook-and-loop fastener 34 and strap members 22 may be elastic.

As shown in FIGS. 2-4, bladder assemblies 50 each include an elongated bladder body 52. In an exemplary embodiment, each bladder assembly 50, i.e. each bladder assembly body 52, is structured to be selectively filled with, or emptied of, a fluid. That is, each bladder assembly body 52 is made from a flexible, non-porous material, such as, without limitation, a rubber material, a polymer (e.g., silicone), or a sealed fabric, and may be filled with a fluid medium. The fluid medium may be a gas, such as, without limitation, air, a liquid, such as, without limitation, water, a saline solution, or mineral oil, another suitable material that is able to flow, such as a gel, or any combination of such fluids. The fluid medium may be heated or chilled if desired.

Bladder assembly bodies 52 include an elongated tubular member 60 and an elongated, substantially planar membrane 62. Bladder assembly membrane 62 has a greater width than the cross-sectional area of bladder assembly tubular member 60. Bladder assembly membrane 62 extends through bladder assembly tubular member 60. In the exemplary embodiment, bladder assembly membrane 62 bisects bladder assembly tubular member 60. In this configuration, bladder assembly membrane 62 has an internal portion 64, disposed within bladder assembly tubular member 60, as well as first and second lateral portions 66, 68. Bladder assembly membrane first and second lateral portions 66, 68 are disposed outside of bladder assembly tubular member 60.

In the exemplary embodiment, bladder assembly tubular member 60 has a generally circular cross-section and bladder assembly membrane first and second lateral portions 66, 68 extend radially from opposite sides of bladder assembly tubular member 60. Bladder assembly membrane 62 has at least one opening 70 structured to allow fluid communication therethrough. Bladder assembly membrane at least one opening 70 is disposed on bladder assembly membrane internal portion 64. In this configuration, fluid may pass through bladder assembly membrane 62 and fill the space on both sides of bladder assembly membrane 62.

In the exemplary embodiment, bladder assembly membrane internal portion 64 has a sufficient rigidity so as to maintain a substantially uniform distance between the strap member body first and second portions 26A, 26B, discussed below. The rigidity of bladder assembly membrane internal portion 64 also assists in directing the force created by inflation of bladder assembly 30 inward to support patient's head 1.

In the exemplary embodiment shown in FIG. 2, strap member body 26 is bifurcated having a first portion 26A and a second portion 26B. Strap member body first and second portions 26A, 26B are elongated and have a width that is about twice as wide as bladder assembly membrane first and second lateral portions 66, 68. In this configuration, each strap member body first or second portions 26A, 26B may be folded over an associated bladder assembly membrane first or second lateral portions 66, 68. Strap member body first and second portions 26A, 26B may then be bonded to the associated bladder assembly membrane first or second lateral portions 66, 68 by any known device or process. That is, the bonding device or process may be, but is not limited to, an adhesive, heat bonding, sonic welding, stitching and overmolding.

Alternatively, as shown in FIG. 3, a single piece strap member body 26 may have a sufficient width to extend under bladder assembly tubular member 60 and bladder assembly membrane first and second lateral portions 66, 68. In this configuration, strap member body 26 is disposed between the patient's face and bladder assembly 50. In another embodiment, shown in FIG. 4, a single piece strap member body 26 may have a sufficient width to extend under bladder assembly tubular member 60 and bladder assembly membrane first and second lateral portions 66, 68 as well as an additional width so as to allow the lateral edges of strap member body 26 to be folded over bladder assembly membrane first and second lateral portions 66, 68.

As discussed below, web 24 of strap members 22 may be separate or interconnected. If strap members 22 are separate, each bladder assembly 50 includes a valve assembly 80. Valve assembly 80 (FIG. 2) is structured to be selectively closed or open. When valve assembly 80 is open, bladder assembly body 52 is in fluid communication with a location outside the bladder assembly. That is, fluid from outside bladder assembly body 52 may pass through valve assembly 80 into bladder assembly body 52.

In one embodiment, not shown, valve assembly 80 is a simple opening with a plug, as typically associated with inflatable toy such as, but not limited to beach balls. In another embodiment, not shown, a hand pump (not shown) may be coupled to valve assembly 80. Valve assembly 80 as shown in the exemplary embodiment in FIG. 2 is structured to be coupled to, and in fluid communication with, pressure generating device 4. That is, a patient may couple line 6 to valve assembly 80 and use the pressurized fluid generated by pressure generating device 4 to fill bladder assembly 50. Pressure generating device 4 may remain coupled to, and in fluid communication with, bladder assembly 50 while patient interface device 8 is in use. In an exemplary embodiment, pressure generating device 4 is to fill bladder assembly 50 then decoupled therefrom.

The present invention further contemplates that the bladder assembly may define a portion of the gas carrying conduit that carries a flow of gas from the pressure generating device to patient sealing assembly 12. That is, line 6 may be provided in fluid communication with the bladder assembly and a portion of the bladder assembly may be in fluid communication with the patient sealing assembly, thus delivering a flow of gas to the airway of the user.

Figure 5:
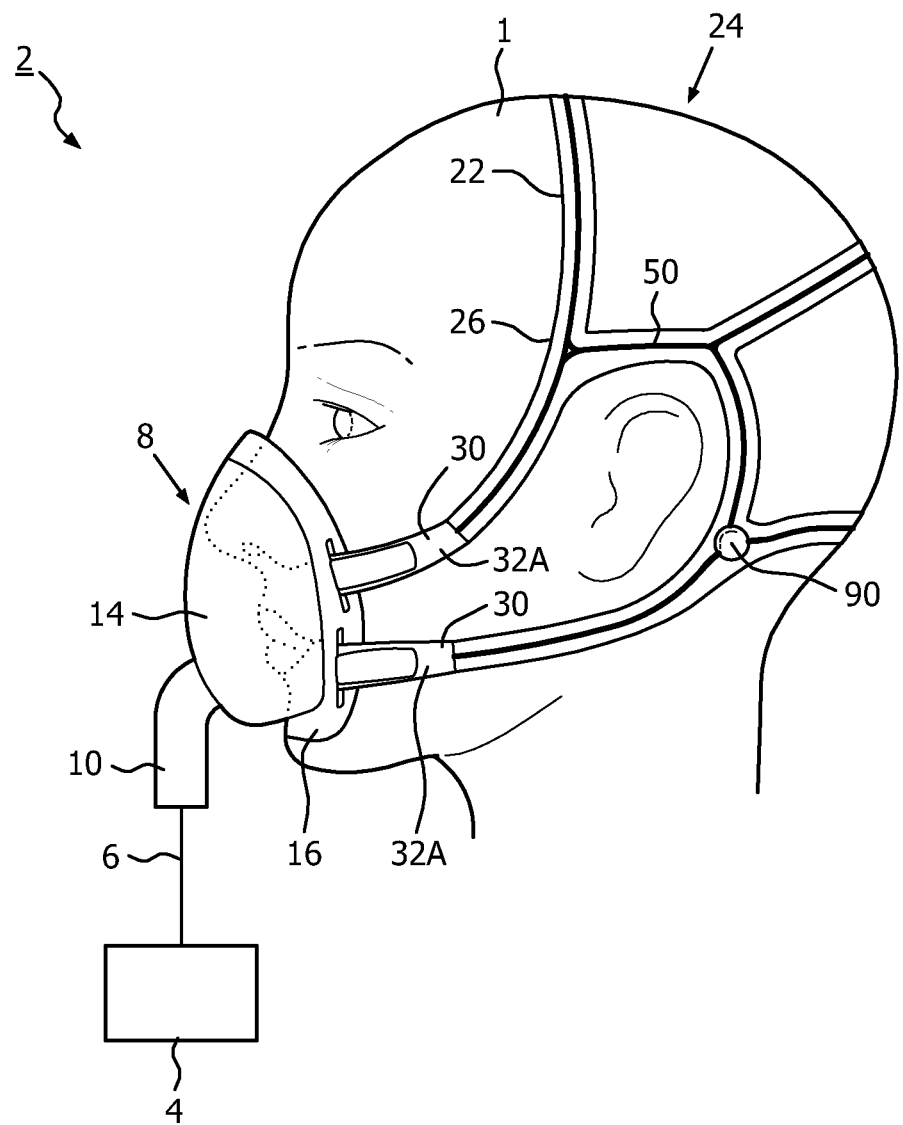
FIG. 5 is a side elevational view of a patient interface device according to an alternative exemplary embodiment of the present invention that may be employed in the system of FIG. 1.

As shown in FIG. 5, in an exemplary embodiment bladder assembly 50 includes a pump 90. Pump 90 is structured to incrementally pass fluid from a location outside bladder assembly 50 into associated bladder assembly body 52. Pump 90 may be a miniature pump such as, but not limited to, a miniature pump used in conjunction with athletic footwear. Such a pump 90 may be fixed to bladder assembly body 52. In this configuration, pump 90 includes a valve assembly 80. Alternatively, a removable pump 90 may be temporarily coupled to bladder assembly body 52 and, as described above, valve assembly 80 is part of bladder assembly 50.

FIGS. 1, and 5-9 show various patterns that web 24 may form. It is noted that other patterns are also possible. Initially, it is noted that web 24 may provide for independent or interconnected strap members 22. It is understood that when strap members 22 are independent, each strap member 22, and more specifically each bladder assembly 50, must include a valve assembly 80, and possible a pump 90, as described above. When strap members 22 are interconnected, bladder assemblies 50 may also be interconnected. That is, when strap members 22 are interconnected bladder assemblies 50 may be in fluid communication with each other. It is understood that when bladder assemblies 50 are in fluid communication with each other, a single valve assembly 80, or pump 90, may be used to inflate/deflate all bladder assemblies 50 simultaneously.

Bladder assemblies 50 may be placed in fluid communication with each other by coupling, while in fluid communication, the ends of various bladder assembly bodies 52 together. Alternatively, coupling conduits 53, which may not include the elements of bladder assembly bodies 52, may be used to couple various bladder assembly bodies 52 and to provide fluid communication. In the exemplary embodiment, coupling conduits 53 are tubular members made from a soft, flexible material, such as, but not limited to, the materials identified above and used for bladder assembly bodies 52.

As shown in FIG. 1 web 24 includes two strap members 22 that are not interconnected. Each strap member 22 extends, generally, in an arc whereby web 24, when inflated, i.e. when bladder assemblies 50, and more specifically bladder assembly bodies 52, are substantially filled with fluid, defines a first, three-dimensional configuration. In the first configuration, the contours of the arcs defined by strap members 22, and, more specifically, by bladder body/bodies 52. The contours of the arcs defined by strap members 22 are shaped to enclose a patient's head. Moreover, strap members 22 may be custom formed for each patient. In the exemplary embodiment, web 24 is sized and shaped so as to not place an uncomfortable pressure on the patient's head 1. Thus, web 24 is a substantially rigid web 24 and, more broadly, headgear assembly 20 is a substantially rigid headgear assembly 20. That is, web 24, or broadly headgear assembly 20, provides a semi-rigid structure that positions patient sealing assembly 12 adjacent a patient's nose and mouth without applying an uncomfortable pressure to the patient's head 1.

This type of fit is accomplished by not drawing patient sealing assembly 12 too tightly against the patient's face. Further, an advantage of a substantially rigid web 24, i.e. headgear assembly 20, is avoiding compression of the patient's head 1 in a manner similar to an all elastic headgear. It is noted that even if coupling 30 includes elastic members, such elastic members would not have a sufficient bias to pull headgear assembly 20 uncomfortably toward the patient's head 1. That is, substantially rigid web 24, i.e. headgear assembly 20, would maintain its three dimensional shape while pulling patient sealing assembly 12 toward web 24, but this would not simultaneously substantially deform web 24 so as to compress web 24 against patient's head 1.

Thus, substantially rigid web 24 is structured to "maintain a patient sealing assembly in a selected relationship relative to the patient's face," which, as used herein, means that patient sealing assembly 12 is disposed adjacent a patient's nose and mouth without the web 24 being biased toward the patient's head 1. That is, a headgear made from elastic members, or substantially from elastic members, biases the elastic web (not shown) toward the patient's head 1. It is further noted that "maintaining patient sealing assembly in a selected relationship relative to the patient's face" is useful when patient sealing assembly 12 includes an inflatable cushion 16, or an otherwise deformable cushion 16, structured to maintain a generally specific shape. That is, such cushions 16 are structured to engage a patient's face with a selected pressure. An all elastic heardgear, or a similar non-rigid headgear, e.g. tension members or straps that are tightened, may pull the cushion 16 too tightly against the patient's face, thereby decreasing its efficacy.

Web 24 may also be placed in a second, collapsed configuration. That is, in the second, collapsed configuration bladder assemblies 50 are deflated, i.e. when bladder assemblies 50, and more specifically bladder assembly bodies 52, are substantially empty. In this configuration, strap members 22 are flexible and may be folded, compressed, and otherwise manipulated into a generally flat or compressed pattern. Thus, web 24 may, for example, be compressed and placed within patient sealing assembly 12. Thus, headgear assembly 20 may be stored in the second collapsed configuration.

It is understood that for each of web 24 configurations discussed below, web 24 may always be placed in either the first, three-dimensional configuration or the second, collapsed configuration. That is, when each bladder assembly 50 is substantially filled with a fluid, web 24 defines a first, three-dimensional configuration, and, when each bladder assembly 50 is substantially emptied of fluid, web 24 defines a second, collapsed configuration. Further, as the Figures disclose a side view of the patient's head 1, it is understood that web 24 is typically symmetrical and has a similar appearance when viewed from the other side of the patient's head 1.

As shown in FIG. 5, web 24 includes a plurality of interconnected strap members 22. As discussed above, bladder assemblies 50 in this configuration are in fluid communication. Thus, a single bladder assembly 50 has a valve assembly 70. When a bladder assembly 50 having the valve assembly 70 is inflated, the fluid is passed to the other bladder assemblies 50. Further, as shown, coupling device flexible material 32A is elastic. Thus, in this embodiment, when web 24 is in the first, three-dimensional configuration, web 24 is shaped to the patient's head 1 (i.e. web 24 does not place an uncomfortable pressure on the patient's head 1) and positions patient sealing assembly 12 adjacent the patient's nose and mouth. Further, the elastic material of coupling device 30 draws patient sealing assembly 12 toward the patient's face thereby enhancing the seal between patient sealing assembly 12 and the patient's face while limiting the pressure on the patient's head 1.

Figure 6:
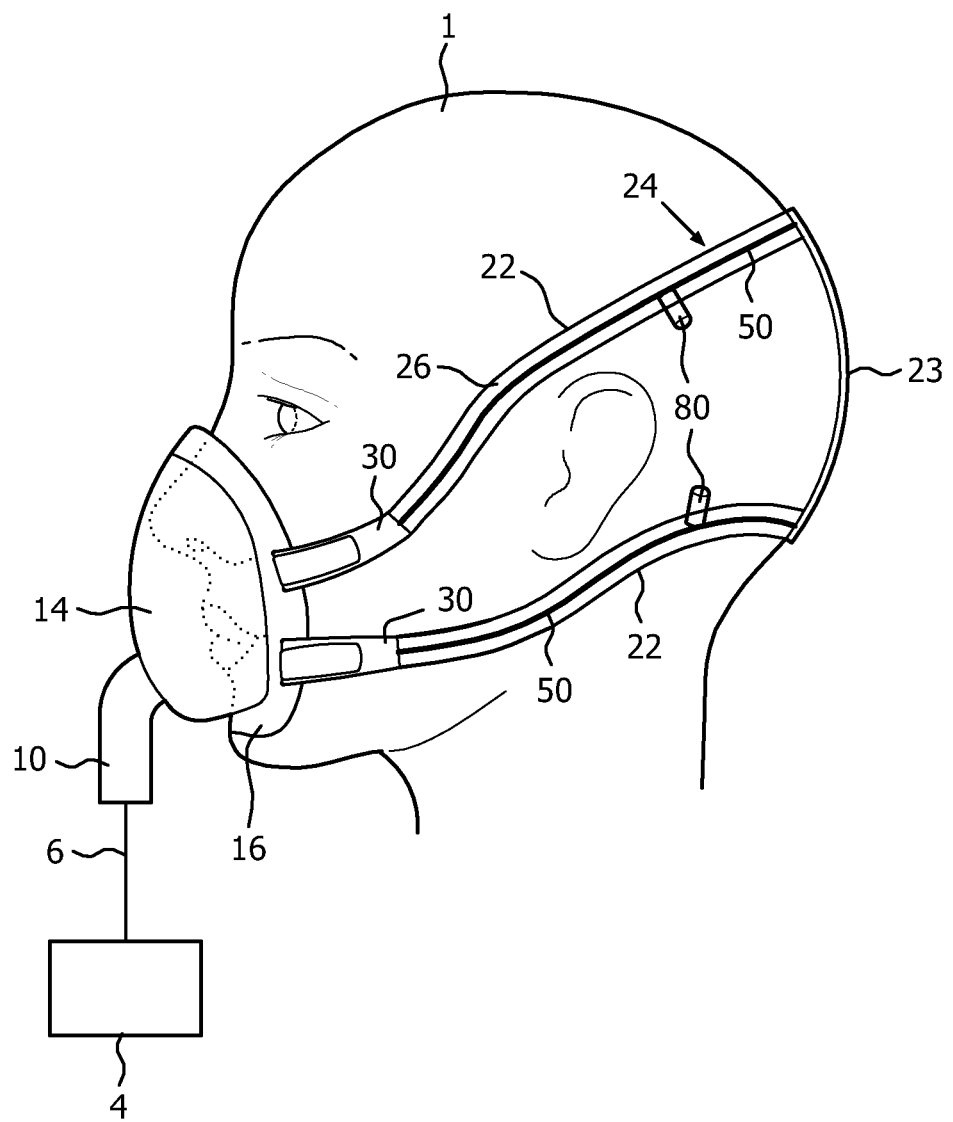
FIG. 6 is a side elevational view of a patient interface device according to an alternative exemplary embodiment of the present invention that may be employed in the system of FIG. 1.

As shown in FIG. 6, web 24 includes both strap members 22 and a band 23. Band 23 may be rigid, or semi-rigid. In this configuration, band 23 maintains strap members 22 in a selected spacing from each other. In the exemplary embodiment, any rigid bands 23 are of a relatively short length so that web 24 may be placed in the second, collapsed configuration.

Figure 7:
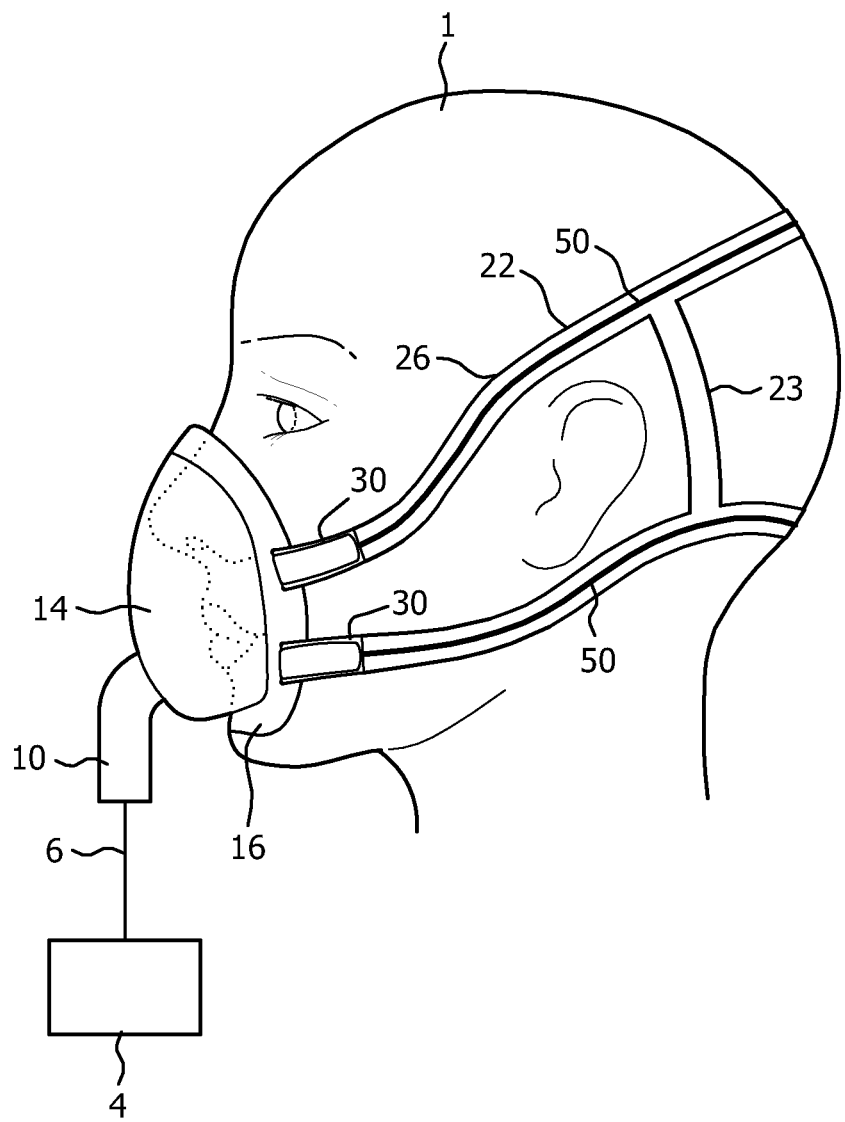
FIG. 7 is a side elevational view of a patient interface device according to an alternative exemplary embodiment of the present invention that may be employed in the system of FIG. 1.

As shown in FIG. 7, web 24 includes both strap members 22 and a bands 23. Band 23 may be flexible. In this configuration, bands 23 prevents strap members 22 from moving beyond a selected spacing from each other.

Figure 8:
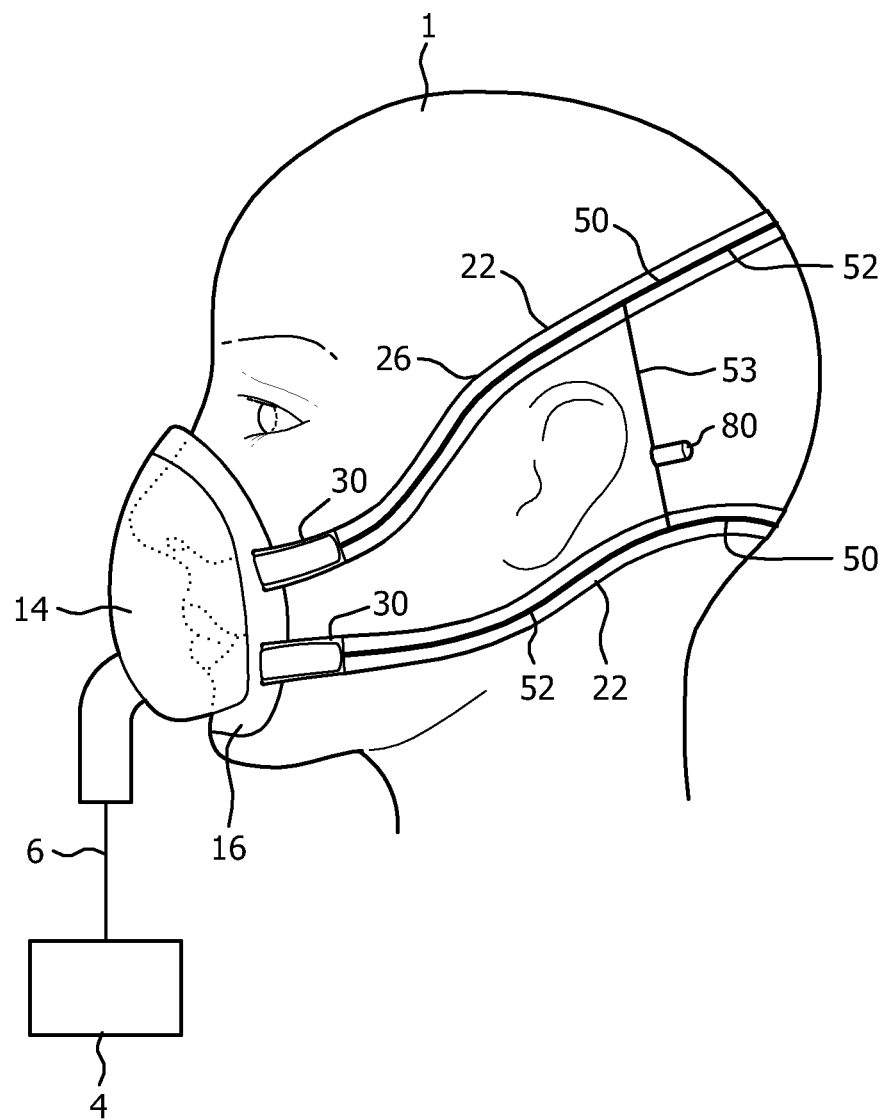
FIG. 8 is a side elevational view of a patient interface device according to another alternative exemplary embodiment of the present invention that may be employed in the system of FIG. 1.

As shown in FIG. 8, web 24 includes two separate strap members 22, each having a bladder assembly 50, wherein bladder assemblies 50 are coupled by a coupling conduit 53. The coupling conduit 52 does not have a strap member body 26. A valve 80 is shown disposed on the coupling conduit 53.

Figure 9:
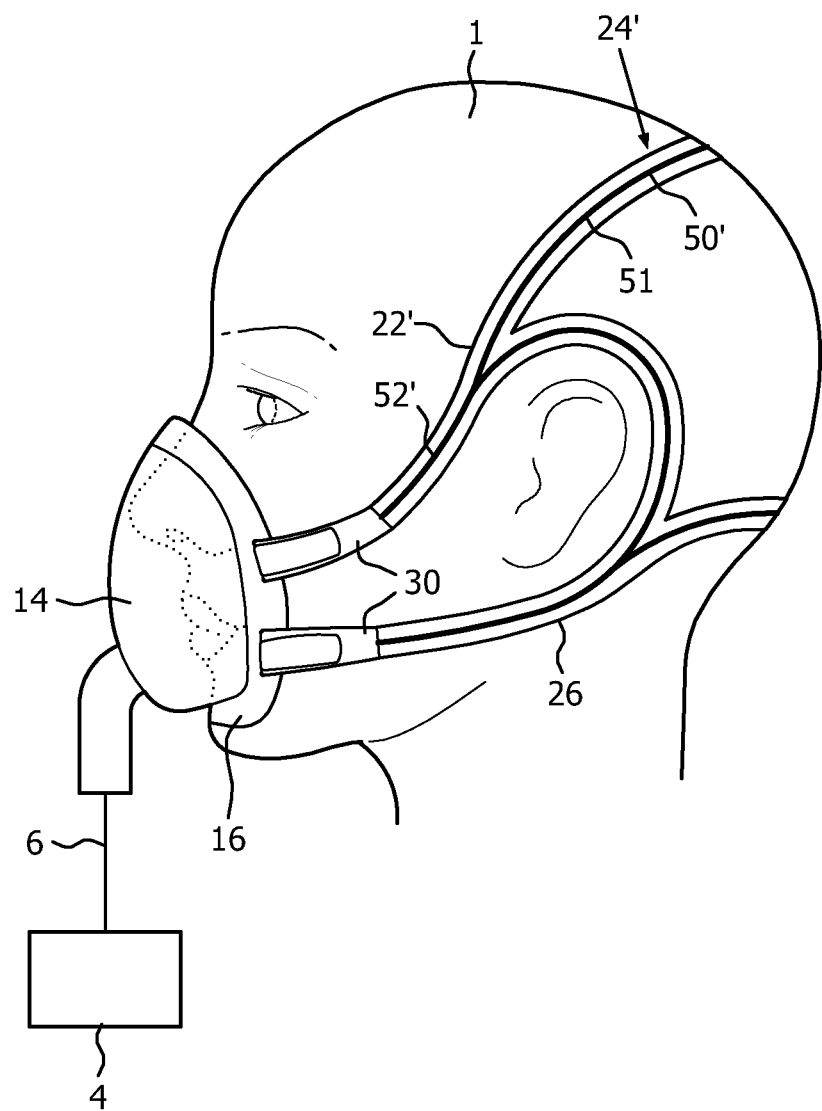
FIG. 9 is a side elevational view of a patient interface device according to an alternative exemplary embodiment of the present invention that may be employed in the system of FIG. 1.

In an alternate embodiment, shown in FIG. 9, headgear assembly 20' provides a semi-rigid web 24'. That is, rather than having inflatable/deflatable bladder assemblies 50, the alternate embodiment provides for a plurality of bladder assemblies 50' filled with a gel 51. Gel 51 allows web 24 for to be semi-rigid. As used herein, "semi-rigid" means capable of maintaining a three dimensional shape while being collapsible under pressure. In this embodiment, there is no need for a valve assembly 80 or a pump 90 as gel 51 is maintained in bladder assembly bodies 52'. With the exception of valve assembly 80 and pump 90, strap members 22' of this embodiment are substantially similar to the embodiment discussed above and like reference numbers, followed by a "'" are utilized.

The semi-rigid embodiment of web 24' will remain in a first, three-dimensional configuration until acted upon by a patient. That is, the patient may manipulate web 24' manually so as to flatten web 24'. Once collapsed, web 24' will tend to remain collapsed. Thus, for example, web 24' may be collapsed and placed in a small pouch or other enclosure. Semi-rigid web 24' will remain in the collapsed configuration until it is placed in an open space. The patient may manipulate semi-rigid web 24' to assist semi-rigid web 24' in returning to the first, three-dimensional configuration.

Figure 10:
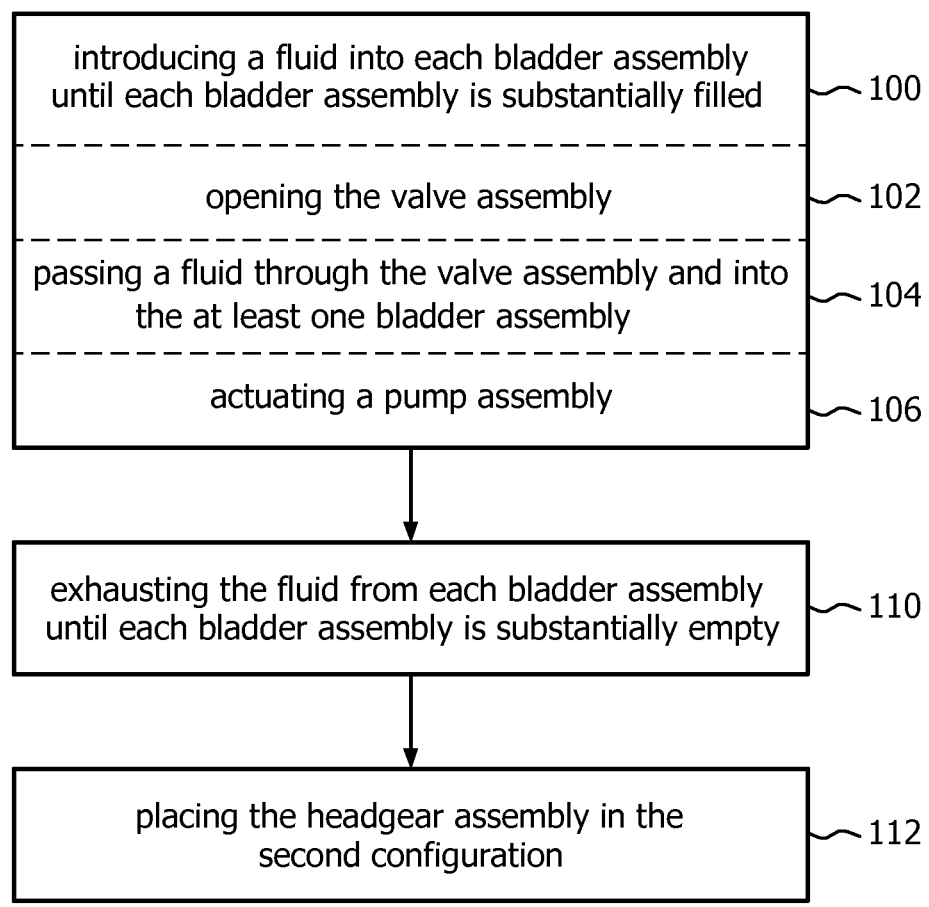
FIG. 10 is a flow chart of the steps for the method of using the a patient interface device.

As shown in FIG. 10, operation of patient interface device 8, and more specifically headgear assembly 20, is as follows. Assuming bladder assemblies 50 are in the collapsed, second configuration initially, a patient performs the 100 step of introducing a fluid into each bladder assembly until each bladder assembly is substantially filled. The 100 step of introducing a fluid into each bladder assembly until each bladder assembly is substantially filled may include the 102 step of opening valve assembly 80 and the 104 step of passing a fluid through the valve assembly and into the at least one bladder assembly 50. Further, the 100 step of introducing a fluid into each bladder assembly until each bladder assembly is substantially filled may include the 106 step of actuating pump 90 whereby fluid from a location outside bladder assembly 50 is incrementally passed into each bladder assembly 50. The method includes the further 110 step of exhausting the fluid from each bladder assembly until each bladder assembly is substantially empty. As noted, web 24 may need to be manipulated by the patient to be placed in the second configuration. Accordingly, the method includes the further 112 step of placing headgear assembly 20 in the second configuration.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A patient interface device headgear assembly for supporting a patient sealing assembly, the headgear assembly comprising:
   a plurality of strap members, each strap member including a body, the strap members forming a web;
   at least two of the strap members structured to be coupled to the patient sealing assembly;
   at least two of the strap members in the plurality of strap members each including a bladder assembly; and
   each bladder assembly including a body structured to be selectively filled with, or emptied of, a fluid;
   wherein when each bladder assembly is substantially filled with a fluid, the web defines a first, three-dimensional configuration, and, when each bladder assembly is substantially emptied of fluid, the web defines a second, collapsed configuration;
   wherein each bladder assembly body includes an elongated tubular member and an elongated, substantially planar membrane, the membrane having a greater width than that of the cross-sectional area of the tubular member, the membrane extending through the tubular member whereby the membrane has an internal portion within the tubular member and first and second lateral portions of the membrane disposed outside the tubular member; and
   wherein the membrane having at least one opening structured to allow fluid communication, the opening disposed on the membrane internal portion; and
   each bladder associated strap body being coupled to at least one of the first and second lateral membrane portions of the associated bladder assembly.

2. The headgear assembly of claim 1, wherein: each bladder-associated strap body is bifurcated having a first portion and a second portion; the strap member body first and second portions having a width that is about twice as wide as bladder assembly membrane first and second lateral portions; and wherein each strap member body first or second portions may be folded over an associated bladder assembly membrane first or second lateral portions.

3. A patient interface device headgear assembly for supporting a patient sealing assembly, the headgear assembly comprising:

a number of bladder assemblies, each bladder assembly including a body structured to be selectively filled with, or emptied of, a fluid;

wherein each bladder assembly body includes an elongated tubular member and an elongated, substantially planar membrane, the membrane having a greater width than that of the cross-sectional area of the tubular member, the membrane extending through the tubular member whereby the membrane has an internal portion within the tubular member and first and second lateral portions of the membrane disposed outside the tubular member;

the membrane having at least one opening structured to allow fluid communication, the opening disposed on the membrane internal portion; and a strap body coupled to at least one of the first and second lateral membrane portions.

4. The headgear assembly of claim 3 further including:

a plurality of strap members;

the strap members forming a web;

the strap members including the strap body coupled to at least one of the first and second lateral membrane portions; and wherein when each bladder assembly is substantially filled with a fluid, the web defines a first, three-dimensional configuration, and, when each bladder assembly is substantially emptied of fluid, the web defines a second, collapsed configuration.

5. The headgear assembly of claim 4 wherein wherein the bladder assembly bodies are in fluid communication with each other;

whereby all the bladder assembly bodies are substantially filled, or substantially emptied, simultaneously.

6. The headgear assembly of claim 4 wherein:

at least one bladder assembly includes a valve assembly;

the valve assembly structured to be selectively closed or open; and wherein, when the valve assembly is open, the at least one bladder assembly is in fluid communication with a location outside the bladder assembly.

7. The headgear assembly of claim 4 wherein:

each said strap member has at least one layer of a flexible material; and each bladder assembly body being coupled to an associated strap member with a longitudinal axis of each bladder body extending generally parallel to a longitudinal axis of the associated strap member.

8. A patient interface device headgear assembly for supporting a patient sealing assembly, the headgear assembly comprising:

a number of bladder assemblies, each bladder assembly including a body structured to be selectively filled with, or emptied of, a fluid;

wherein each bladder body includes an elongated tubular member and an elongated, substantially planar membrane, the membrane having a greater width than that of the cross-sectional area of the tubular member, the membrane extending through the tubular member whereby the membrane has an internal portion within the tubular member and first and second lateral portions of the membrane disposed outside the tubular member;

a strap body coupled to at least one of the first and second lateral membrane portions; and wherein at least one bladder assembly includes a pump, the pump structured to incrementally pass fluid from a location outside the bladder assembly into the associated bladder assembly.

* * * * *